(12) United States Patent
Hokkanen et al.

(10) Patent No.: US 8,877,963 B2
(45) Date of Patent: Nov. 4, 2014

(54) PRODUCTION OF ACETIC ACID WITH HIGH CONVERSION RATE

(75) Inventors: Brian W. Hokkanen, Houston, TX (US); Michael Nutt, Pearland, TX (US); Tianshu Pan, Houston, TX (US); Ronald David Shaver, Houston, TX (US); G. Paull Torrence, League City, TX (US)

(73) Assignee: Celanese International Corporation, Dallas, TX (US)

( * ) Notice: Subject to any disclaimer, the term of this patent is extended or adjusted under 35 U.S.C. 154(b) by 704 days.

(21) Appl. No.: 13/231,205

(22) Filed: Sep. 13, 2011

(65) Prior Publication Data

US 2012/0083623 A1 Apr. 5, 2012

Related U.S. Application Data

(63) Continuation-in-part of application No. 12/892,348, filed on Sep. 28, 2010, now Pat. No. 8,394,988.

(51) Int. Cl.
*C07C 51/12* (2006.01)
*C07C 51/44* (2006.01)

(52) U.S. Cl.
CPC .................. *C07C 51/12* (2013.01); *C07C 51/44* (2013.01)
USPC .......................................................... 562/519

(58) Field of Classification Search
CPC ................................ C07C 51/12; C07C 51/44
USPC .................................................. 562/517, 519
See application file for complete search history.

(56) References Cited

U.S. PATENT DOCUMENTS

| | | | |
|---|---|---|---|
| 3,769,329 A | 10/1973 | Paulik et al. | |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,334,755 A | 8/1994 | Yoneda et al. | |
| 5,380,929 A | 1/1995 | Erpenbach et al. | |
| 5,391,821 A | 2/1995 | Koyama et al. | |
| 5,599,976 A | 2/1997 | Scates et al. | |
| 5,672,744 A | 9/1997 | Kagotani et al. | |
| 5,683,492 A | 11/1997 | Hesse et al. | |
| 5,696,284 A | 12/1997 | Baker et al. | |
| 5,731,252 A | 3/1998 | Warner et al. | |
| 5,840,969 A | 11/1998 | Joensen | |
| 5,877,347 A | 3/1999 | Ditzel et al. | |
| 5,877,348 A | 3/1999 | Ditzel et al. | |
| 5,883,295 A | 3/1999 | Sunley et al. | |
| 5,883,764 A | 3/1999 | Pinarbasi | |
| 5,917,089 A | 6/1999 | Howard | |
| 5,932,764 A | 8/1999 | Morris et al. | |
| 5,942,460 A | 8/1999 | Garland et al. | |
| 6,140,535 A | 10/2000 | Williams | |
| 6,143,930 A | 11/2000 | Singh et al. | |
| 6,153,792 A | 11/2000 | Leet et al. | |
| 6,232,352 B1 | 5/2001 | Vidalin | |
| 6,339,171 B1 | 1/2002 | Singh et al. | |
| 6,462,231 B1 | 10/2002 | Yanagawa et al. | |
| 6,617,471 B2 | 9/2003 | Zoeller et al. | |
| 6,627,770 B1 | 9/2003 | Cheung et al. | |
| 6,657,078 B2 | 12/2003 | Scates et al. | |
| 6,727,380 B2 | 4/2004 | Ellis et al. | |
| 7,005,541 B2 | 2/2006 | Cheung et al. | |
| 7,115,772 B2 | 10/2006 | Picard et al. | |
| 7,202,382 B2 | 4/2007 | Muskett | |
| 7,208,624 B2 | 4/2007 | Scates et al. | |
| 7,223,886 B2 | 5/2007 | Scates et al. | |
| 7,473,800 B2 | 1/2009 | Hosono et al. | |
| 7,678,940 B2 | 3/2010 | Miura et al. | |
| 2003/0199711 A1 | 10/2003 | Broussard et al. | |
| 2005/0165251 A1 | 7/2005 | Muskett | |
| 2008/0287706 A1 | 11/2008 | Powell et al. | |
| 2008/0293966 A1 | 11/2008 | Scates et al. | |
| 2009/0107833 A1 | 4/2009 | Warner | |
| 2009/0270650 A1 | 10/2009 | Patt | |
| 2009/0270651 A1 | 10/2009 | Zinobile et al. | |
| 2010/0069514 A1 | 3/2010 | Gracey et al. | |

FOREIGN PATENT DOCUMENTS

| | | |
|---|---|---|
| CN | 1537840 | 10/2004 |
| CN | 101439256 A | 5/2009 |
| JP | 8-188547 A | 7/1996 |
| WO | WO 2007/107724 A1 | 9/2007 |
| WO | WO 2012/050846 A1 | 4/2012 |

OTHER PUBLICATIONS

International Preliminary Report on Patentability for PCT/US2011/053539 mailed Nov. 26, 2012.
International Written Opinion mailed Oct. 17, 2012 in corresponding International Application No. PCT/US2011/053369.
International Invitation to Pay Fees mailed Nov. 29, 2012 in corresponding International Application PCT/US2012/052829.
J. H. Jones (2002), "The Cativa™ Process for the Manufacture of Acetic Acid", Platinum Metals Review, 44(3): 94-105.

(Continued)

*Primary Examiner* — Yevegeny Valenrod

(57) ABSTRACT

The present invention is to a process for producing acetic acid comprising the step of reacting a carbon monoxide feed and methanol and/or a methanol derivative in a first reactor to produce a crude acetic acid product. The carbon monoxide may comprise less than 99.5 mol % carbon monoxide. The process further comprises the step of purging a carbon monoxide purge stream comprising a first amount of residual carbon monoxide and one or more impurities. Preferably, the first amount is greater than 20 mol %. The process further comprises the step of separating the crude acetic acid product into at least one derivative stream comprising a second amount of residual carbon monoxide. The process further comprises the step of reacting at least a portion of the second amount of residual carbon monoxide and methanol and/or a methanol derivative in a second reactor to produce additional acetic acid.

22 Claims, 5 Drawing Sheets

(56) References Cited

OTHER PUBLICATIONS

Michael Gauβ, et al., Applied Homogeneous Catalysis with Organometallic Compounds: A Comprehensive Handbook in Two Volume, Chapter 2.1, pp. 27-200, (1st ed., 1996).

Noriyuki Yoneda and Yasuo Hosono (2004); "Acetic Acid Process Catalyzed by Ionically Immobilized Rhodium Complex to Solid Resin Support", Journal of Chemical Engineering of Japan, vol. 34, No. 4, 536-545.

International Search Report and Written Opinion mailed on Jan. 25, 2012 in corresponding International Application No. PCT/US11/53539.

International Search Report and Written Opinion mailed on Jan. 25, 2012 in corresponding International Application No. PCT/US2011/053369.

PRODUCTION OF ACETIC ACID WITH HIGH CONVERSION RATE

CROSS-REFERENCE TO RELATED APPLICATIONS

This application is a continuation-in-part if and claims priority to U.S. application Ser. No. 12/892,348, filed on Sep. 28, 2010, the disclosure of which is hereby incorporated by reference.

FIELD OF THE INVENTION

This invention relates to processes for producing acetic acid from carbon monoxide and in particular to improved processes that react residual carbon monoxide to form additional acetic acid, thus improving overall carbon monoxide efficiency.

BACKGROUND OF THE INVENTION

A widely used and successful commercial process for synthesizing acetic acid involves the catalyzed carbonylation of methanol with carbon monoxide. Catalysts used in this reaction typically contain rhodium and/or iridium as well as a halogen promoter, for example methyl iodide. The carbonylation reaction may be conducted by continuously bubbling carbon monoxide through a liquid reaction medium in which the catalyst is dissolved. In addition to the catalyst, the reaction medium also may comprise methyl acetate, water, methyl iodide and the catalyst. Conventional commercial processes for carbonylation of methanol include those described in U.S. Pat. Nos. 3,769,329, 5,001,259, 5,026,908, and 5,144,068, the disclosures of which are hereby incorporated by reference. Also, U.S. Pat. No. 6,617,471, the disclosure of which is hereby incorporated by reference, discloses a vapor-phase carbonylation method for producing esters and carboxylic acids from reactants comprising lower alkyl alcohols, lower alkyl alcohol generating compounds, and mixtures thereof. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the disclosure of which is hereby incorporated by reference.

In the methanol carbonylation reaction, carbon monoxide, by-product gases, and feed impurities, e.g., hydrogen, nitrogen, argon, methane, and carbon dioxide, that are initially present in the carbon monoxide feed may build up in the reactor as the crude acetic acid product is formed. To improve overall reaction and catalyst efficiency and to prevent the build-up of these gases, a purge stream, e.g., an off-gas stream, is typically vented from the reactor. The vented purge stream may comprise carbon monoxide, inerts, volatile halogen promoters, acetic acid, water, unreacted methanol, methyl acetate and/or feed impurities. Typically, the purge stream as a whole is withdrawn directly from the reactor, e.g., the purge stream components are not withdrawn individually. Because the carbon monoxide in the purge stream is vented from the process, the same is not converted to acetic acid. As such, this loss of carbon monoxide contributes to a reduction in a carbon monoxide efficiency of the system. In addition to the carbon monoxide lost via the purge stream, residual carbon monoxide that remains in the crude acetic acid product after the primary reaction often is separated and purged, which further contributes to reductions in carbon monoxide efficiency. Accordingly, to improve overall carbon monoxide efficiency, conventional methanol carbonylation systems have attempted to reduce the size of the vented purge stream and the amount of carbon monoxide therein.

Even though the sizes of conventional purge streams are often minimized, the purge stream still may be processed to recover and/or utilize the components thereof. For example, the purge stream, once withdrawn, may be processed to recover volatile halogen promoters, acetic acid, water, unreacted methanol, and/or methyl acetate, which may in turn be recycled to the reactor. As another example, the small amount of carbon monoxide in the vent stream may be used to enhance catalyst stability, e.g., to reduce catalyst precipitation, in the units of the system.

As another example, U.S. Pat. No. 5,917,089 discloses that a purge stream, e.g., "off-gas" from the reactor may be fed directly to a second reactor, along with fresh methanol, to produce additional carbonylation product, i.e. acetic acid. The off-gas, as known in the art, is not a derivative stream. Although the carbon monoxide in the purge stream may be converted and efficiency may be slightly improved in this case, the amount of carbon monoxide available for catalyst stabilization is lessened.

Also, as noted above, conventional carbon monoxide feed impurities are also vented via the off-gas. Because the off-gas stream is vented from the reactor as a whole, conventional processes keep the amount of impurities in the carbon monoxide feed stream as low as possible, e.g., to minimize the loss of carbon monoxide that would accompany the unwanted impurities that are purged. Accordingly, conventional carbonylation processes often employ high purity carbon monoxide feed streams, which contain very low amounts of impurities. As a result of the very low amount of impurities, only smaller amounts of the off gas need to be vented from the reactor.

Generally speaking, the crude acetic acid product from the reactor is then processed via a purification train to remove impurities and provide a high quality acetic acid product. The purification train may include several vents, which purge non-condensable gases. The gases that are purged via the purification train vents may be processed in a recovery unit to recover light boiling point components, such as the halogen promoter, as described in US Publication No. 2008/0293966, the entire content and disclosure of which is hereby incorporated by reference. In most cases, at least a portion of the non-condensable gases, e.g., carbon monoxide, whether or not they pass through the recovery unit, are typically purged or flared. As noted above, this loss of residual carbon monoxide contributes to additional reductions in carbon monoxide efficiency.

Accordingly, in view of these references, the need exists for a methanol carbonylation process that provides 1) an increased amount carbon monoxide available for use as a catalyst stabilizer; and 2) an ability to use a lower purity carbon monoxide feed, while maintaining a high overall carbon monoxide efficiency.

SUMMARY OF THE INVENTION

The present invention is to process for producing acetic acid. In a first embodiment, a process comprises the step of reacting (i) a carbon monoxide feed; and (ii) at least one of methanol and a methanol derivative in a reactor, under conditions effective to produce a crude acetic acid product. In preferred embodiments, the carbon monoxide feed is a lower purity carbon monoxide feed, e.g., a carbon monoxide feed comprising less than 99.5 mol % carbon monoxide. For example, the carbon monoxide feed may comprise from 20 mol % to 99.5 mol % carbon monoxide. The process, in some embodiments, further comprises the step of purging from the first reactor a carbon monoxide purge stream comprising a first amount of residual carbon monoxide and one or more impurities. Preferably, the first amount is greater than 20 mol %, based on the total moles of the purge stream. The process further comprises the step of separating the crude acetic acid product into at least one derivative stream. At least one of the derivative stream(s) comprises residual carbon monoxide, e.g., a second amount of residual carbon monoxide. The process further comprises the step of reacting (i) at least a portion of the second amount of residual carbon monoxide; and (ii) at least one of methanol and a methanol derivative in a second reactor under conditions effective to produce additional acetic acid. As a result of these steps, the inventive process achieves an overall carbon monoxide conversion of at least 95%, based on the total amount of carbon monoxide in the carbon monoxide feed.

In another embodiment, the process comprises the step of reacting (i) the first and second amounts of residual carbon monoxide; and (ii) at least one of methanol and a methanol derivative, in a second reactor under conditions effective to produce additional acetic acid. As a result, in some embodiments, less than 10 mol % of the first and second amounts of residual carbon monoxide, in total, are vented from the process.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
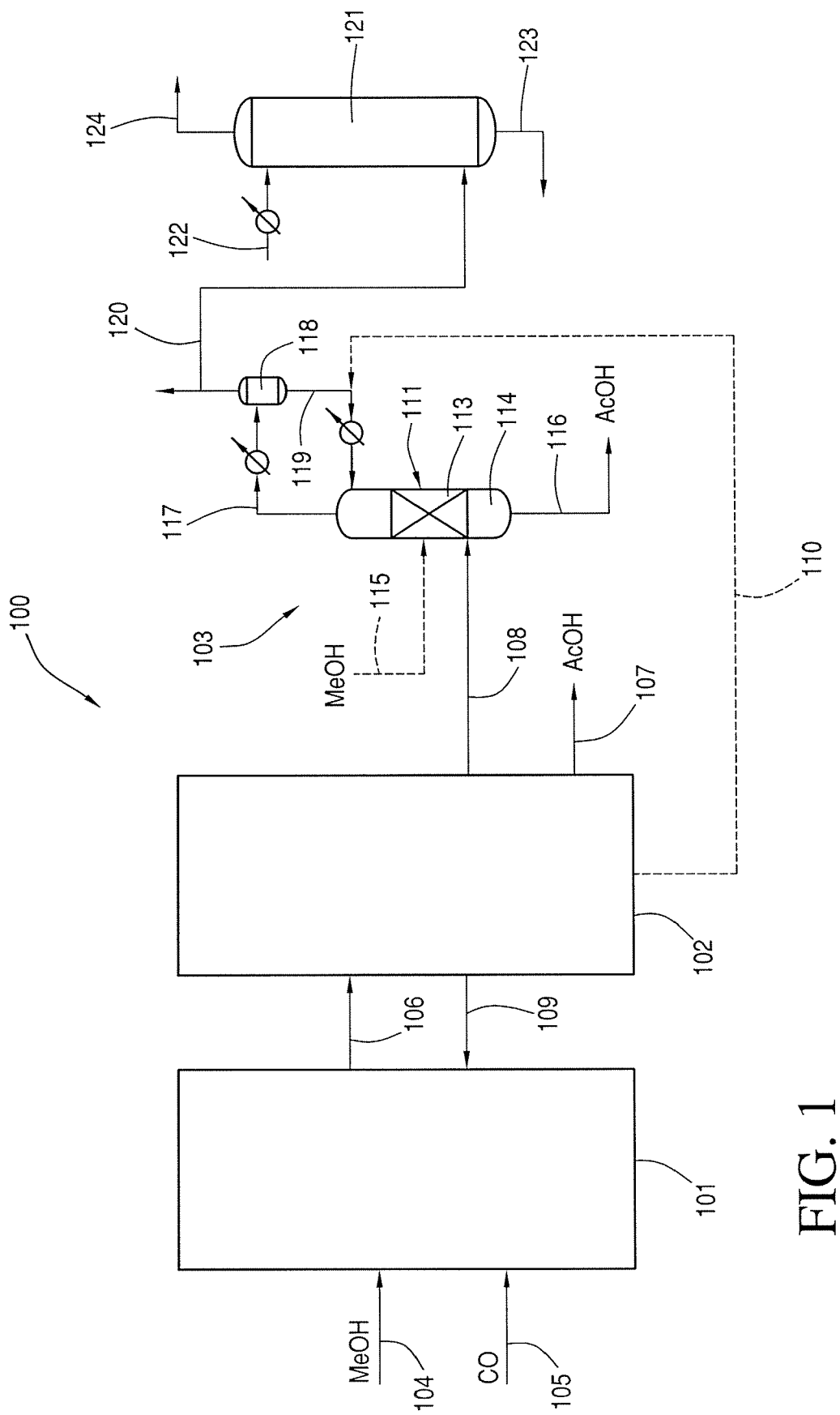
FIG. 1 is a schematic diagram of an exemplary high pressure liquid phase carbonylation secondary reactor for processing a purged derivative stream from an acetic acid purification section in accordance with an embodiment of the present invention.

The present invention generally relates to producing acetic acid from residual or unreacted carbon monoxide that is present either in derivative streams of a crude acetic acid product or in purge streams, e.g., off-gas streams, which are purged from a primary reactor. The derivative stream(s) may be obtained during the purification of the crude acetic acid product. Conventionally, the residual carbon monoxide in the derivative stream(s) is vented, purged and/or goes unutilized. As a result of the present invention's ability to convert residual carbon monoxide into additional acetic acid, higher overall carbon monoxide efficiencies may be obtained. In some embodiments, because the residual carbon monoxide is converted and is not wasted, it is possible to purge larger carbon monoxide-containing purge stream(s) from the first reactor, e.g., the primary reactor. Preferably, these purge streams comprise a higher volume percentages of carbon monoxide. As a result of the larger purge stream(s), alone or in combination with the derivative stream(s), the inventive processes provide availability of larger amounts of carbon monoxide for use throughout the carbonylation process, e.g., for catalyst stabilization. These larger amounts of carbon monoxide are achieved without feeding additional carbon monoxide to the system and while still achieving overall carbon monoxide efficiencies equal to or greater than those of conventional carbonylation systems. In addition, because at least a portion of the residual carbon monoxide is converted, the inventive process allows the use of a carbon monoxide feed stream that comprises more impurities than a conventional feed stream. In these cases again, the overall carbon monoxide efficiencies remain equal to or greater than those of conventional carbonylation systems. For example, the inventive carbon monoxide feed streams may comprise less than 99.5 mol % carbon monoxide, e.g., less than 95 mol % or less than 90 mol %. These less pure feeds may allow significant flexibility in raw material procurement.

For purposes of the present application, a separation zone refers to the portion of the process that purifies the crude acetic acid product and/or separates impurities from the crude acetic acid product. In a preferred embodiment, the derivative streams are vented gas streams of the separation zone. The derivative streams exclude conventional "off-gas" streams that are vented from the reactor. In one embodiment, the present invention advantageously increases the overall carbon monoxide efficiency by utilizing the residual carbon monoxide in the derivative streams to form additional acetic acid. Another embodiment of the present invention advantageously reduces the amount of carbon monoxide that is purged or flared, e.g., from the purification and separation section.

The present invention relates to a process for producing acetic acid. In one embodiment, the process comprises the step of reacting (i) a carbon monoxide feed; and (ii) at least one of methanol and a methanol derivative in a reactor, under conditions effective to produce a crude acetic acid product. In one embodiment, the reactor is a first reactor, e.g., a primary reactor. The inventive system may further comprise additional reactor(s), e.g., secondary reactor(s). In preferred embodiments, the carbon monoxide feed is a lower purity carbon monoxide feed (as compared to a conventional carbon monoxide feed stream), e.g., a carbon monoxide feed comprising less than 99.5 mol % carbon monoxide, e.g., less than 95 mol %, less than 90 mol % or less than 60 mol %. As a lower limit, the carbon monoxide feed may comprise more than 10 mol % carbon monoxide, e.g., more than 20 mol %, more than 50 mol % or more than 75 mol %. In terms of ranges, the carbon monoxide feed may comprise from 10 mol % to 99.5 mol % carbon monoxide, e.g., from 50 mol % to 95 mol %, from 75 mol % to 90 mol %, or from 60 mol % to 70 mol %. The lower purity carbon monoxide feeds of the present invention comprise lower amount of carbon monoxide and/or higher amounts of impurities than conventional carbon monoxide feeds. As such, the lower purity carbon monoxide feed streams of the present invention may advantageously present a wide array of previously unavailable procurement options, e.g., lower pricing and increased availability. For example, the carbon monoxide feed streams of the present invention may come from a waste vent stream of hydroformylation, e.g., to form aldehydes from alkenes; from homologation, e.g., to form higher alcohols; from Fischer-Tropsch e.g., to form liquid hydrocarbons processes; from a waste stream from a steel manufacturing process, from gasified biomass, and/or from and other waste stream, e.g., a low sulfur content waste stream. The present invention may employ such lower purity feed streams and still achieve acceptable carbon monoxide efficiencies.

In addition to carbon monoxide, the carbon monoxide feed of the present invention, in some embodiments, further comprises impurities. Exemplary feed impurities include hydrogen, nitrogen, argon, methane, and carbon dioxide. This listing is not exclusive and other impurities may be present. In one embodiment, the carbon monoxide feed stream comprises low amounts of sulfur, e.g., less than 1 mol %, less than 0.1 mol %, or less than 0.01 mol %. In one embodiment, the carbon monoxide feed stream is sulfur-free. Preferably, the carbon monoxide feed comprises at least 0.5 mol % impurities, e.g., at least 5 mol % or at least 10 mol %. As an upper limit, the carbon monoxide feed may comprise less than 80 mol % impurities, e.g., less than 70 mol % or less than 50 mol %. In terms of ranges, the carbon monoxide feed may comprise from 0.5 mol % to 80 mol % impurities, e.g., from 5 mol % to 70 mol % or from 10 mol % to 50 mol %. In one embodiment, the carbon monoxide feed stream comprises from 30 mol % to 50 mol % impurities and from 50 mol % to 70 mol % carbon monoxide. One example of such a stream is a waste stream from a steel manufacturing process.

The process, in some embodiments, further comprises the step of purging from the first reactor a carbon monoxide purge stream comprising (i) a first amount of residual carbon monoxide and (ii) one or more impurities. Preferably, the first amount of residual carbon monoxide is at least 20 mol % residual carbon monoxide, e.g., at least 30 mol % or at least 70 mol %. As an upper limit, the first amount of residual carbon monoxide is less than 95 mol % carbon monoxide, e.g., less than 50 mol % or less than 20 mol %. In terms of ranges, the first amount of residual carbon monoxide may range from 20 mol % to 95 mol % carbon monoxide, e.g., from 30 mol % to 50 mol % Impurities are also present in the purge stream. In one embodiment, the purge stream comprises from 0.5 mol % to 80 mol % impurities, e.g., from 5 mol % to 70 mol % or from 10 mol % to 50 mol %. In one embodiment, the purge stream comprises from 0.5 mol % to 50 mol % hydrogen, e.g., from 1 mol % to 30 mol % or from 1 mol % to 10 mol %. In one embodiment, the purge stream comprises from 0.5 mol % to 20 mol % nitrogen, e.g., from 1 mol % to 10 mol %. In one embodiment, the purge stream comprises from 0.5 mol % to 20 mol % argon, e.g., from 1 mol % to 10 mol %. In one embodiment, the purge stream comprises from 0.5 mol % to 20 mol % methane, e.g., from 1 mol % to 10 mol %. In one embodiment, the purge stream comprises from 0.5 mol % to 30 mol % carbon dioxide, e.g., from 5 mol % to 25 mol %. In one embodiment, the purge stream comprises low amounts of sulfur, e.g., less than 1 mol %, less than 0.1 mol %, or less than 0.01 mol %. In one embodiment, the purge stream is sulfur-free. The purge stream may comprise impurities in concentrations similar to those of the carbon monoxide feed stream.

In a preferred embodiment, the purging maintains a carbon monoxide partial pressure in the reactor at a predetermined level ranging from 0.13 MPa to 1.1 MPa, e.g., from 0.45 MPa to 0.85 MPa or from 0.65 MPa to 0.80 MPa. In terms of lower limits, the purging may maintain a carbon monoxide partial pressure in the reactor above 0.0.13 MPa, e.g., above 0.45 MPa or above 0.65 MPa. In terms of upper limits, the purging may maintain a carbon monoxide partial pressure in the reactor below 1.1 MPa, e.g., below 0.85 MPa, or below 0.80 MPa.

The crude acetic acid product comprises acetic acid and residual carbon monoxide. The residual carbon monoxide may be dissolved and/or entrained in the crude acetic acid product. In one embodiment, the crude acetic acid product comprises residual carbon monoxide in an amount less than 20 mol %, e.g., less than 10 mol %, less than 5 mol %, or less than 3 mol %. In another embodiment, a flashed vapor phase crude acetic acid product has a carbon monoxide partial pressure that is less than 20% of the total pressure of the flashed crude acetic acid product, e.g., less than 10%, less than 5%, or less than 3%. In another embodiment, the flashed crude acetic acid product is at a total pressure of 0.3 MPa has a carbon monoxide partial pressure of less than 0.06 MPa, e.g., less than 0.03 MPa; less than 0.015 MPa; or less than 0.009 MPa. Of course, for carbon monoxide to be reacted with methanol and/or a methanol derivative to form additional acetic acid, some amount of carbon monoxide should be present. For example, the crude acetic acid product may comprise residual carbon monoxide in an amount greater than 0.1 mol %, greater than 0.5 mol % or greater than 1 mol %. In terms of partial pressures, the flashed crude acetic acid product may have a (residual) carbon monoxide partial pressure of at least 0.1% of the total pressure of the flashed crude acetic acid product, e.g., at least 0.5% or at least 1%. For example, where the flashed crude acetic acid product is at 0.3 MPa total pressure, the carbon monoxide partial pressure may be of at least 0.0003 MPa, e.g., at least 0.0015 MPa or at least 0.003 MPa. In addition, the crude acetic acid product may comprise at least 50 mol % acetic acid, e.g., at least 75 mol %, at least 90 mol %, at least 95 mol %, or at least 98 mol %. In other embodiments, the crude acetic acid product may have an acetic acid partial pressure of at least 50% of the total pressure of the crude acetic acid product, e.g., at least 75%, at least 90%, at least 95%, or at least 98%. In terms of ranges, the crude acetic acid product optionally comprises from 0.1 mol % to 20 mol % residual carbon monoxide, e.g., from 0.5 mol % to 10 mol %, or from 1 mol % to 5 mol %; or from 50 mol % to 99.9 mol % acetic acid, e.g., from 60 mol % to 99 mol %, or from 75 mol % to 95 mol %. In terms of partial pressures, the crude acetic acid product optionally has a carbon monoxide partial pressure of from 0.1% to 20% of the total pressure of the crude acetic acid product, e.g., from 0.5% to 10% or from 1% to 5%; and an acetic acid partial pressure of from 50% to 99.9% of the total pressure of the crude acetic acid product, e.g., from 60% to 99% or from 75% to 95%. Optionally, the crude acetic acid product further comprises methyl iodide (liquid and/or vapor), methyl acetate, propionic acid, water, residual catalyst, and acetaldehyde. In one embodiment, the crude acetic acid product may comprise acetic acid, residual catalyst, dissolved and/or entrained carbon monoxide, methyl iodide, methyl acetate, water, permanganate reducing compounds ("PRCs"), and/or other dissolved gases such as carbon dioxide, hydrogen, and methane.

In one embodiment, the process further comprises the step of separating the crude acetic acid product into at least one derivative stream, e.g., a plurality of derivative streams. At least one of the derivative streams, e.g., at least two or at least three of the derivative streams, comprises a second amount of the residual carbon monoxide. The second amount of carbon monoxide is separate and different from the first amount of residual carbon monoxide that is in the off-gas stream. Preferably, the at least one of the derivative streams is a vapor. Residual carbon monoxide includes carbon monoxide that has not reacted in the carbonylation reaction and, as such, remains in the crude acetic acid product and/or in the off-gas.

In one embodiment, the residual carbon monoxide in the derivative stream(s) is entrained in the respective stream. Without being bound by theory, it is believed that the entrainment of the carbon monoxide is due to the carbon monoxide being conveyed through the liquid reaction mixture. In contrast, the typical off-gas stream is a stream that is removed from the vapor built up in the reactor. Thus, the carbon monoxide in conventional off-gas streams typically is not entrained in the stream. In one embodiment, the derivative stream(s) comprise less carbon monoxide than the carbon monoxide fed to the primary reactor. In one embodiment, the derivative stream(s) comprise less than 95 mol % carbon monoxide, e.g., less than 80 mol %, less than 75 mol %, less than 60 mol %, less than 50 mol %, or less than 40 mol %. In another embodiment, the vapor phase derivative stream(s) have a carbon monoxide partial pressure of less than 95% of the total pressure of the vapor phase derivative stream(s), e.g., less than 75%, less than 60%, less than 50%, or less than 40%. In terms of ranges, the derivative stream(s) optionally comprise from 10 mol % to 95 mol % residual carbon monoxide, e.g., from 25 mol % to 75 mol %, or from 40 mol % to 60 mol %. Preferably, the derivative stream(s) comprise from 60 mol % to 70 mol % carbon monoxide. In terms of partial pressures, the derivative stream(s) optionally have a carbon monoxide partial pressure of from 10% to 95% of the total pressure of the derivative stream(s), e.g., from 25% to 75% or from 40% to 60%. In one embodiment, the derivative streams further comprise methanol and/or methanol derivative(s). For example, the derivative stream(s) may further comprise methanol and/or methanol derivatives in an amount less than 50 mol %, e.g., less than 40 mol %, less than 25 mol % or less than 15 mol %. In terms of ranges, the derivative stream(s) may comprise from 5 mol % to 90 mol % methanol and/or methanol derivative, e.g., from 10 mol % to 60 mol %, or from 15 mol % to 30 mol %.

In addition, the process comprises the step of reacting, in a second reactor, (i) at least a portion of the second amount of residual carbon monoxide; and (ii) at least one of methanol and a methanol derivative, e.g., methyl acetate or dimethyl ether, to produce additional acetic acid. The reaction in the second reactor is preferably performed in a fixed bed reactor or a trickle bed reactor. These reactors preferably comprise a catalyst, e.g., a solid phase metal catalyst. The second reactor provides for reaction of residual carbon monoxide, which improves overall process efficiency. As a result of the inventive combination of steps, the inventive process achieves an overall carbon monoxide conversion of at least 95%, e.g., at least 98%, at least 99% or at least 99.5%, based on the total amount of carbon monoxide in the carbon monoxide feed. In a preferred embodiment, when utilizing the inventive secondary reactor, the overall carbon monoxide conversion achieved by the inventive processes (using a low purity carbon monoxide feed) is at least equivalent to the overall carbon monoxide conversions achieved in conventional processes, which employ a high purity carbon monoxide feed stream, but do not utilize a secondary reaction. In preferred embodiments, the overall carbon monoxide conversion achieved by the inventive processes (using a low purity carbon monoxide feed) is at least at least 1% greater than the overall carbon monoxide conversions achieved in conventional processes, which employ a high purity carbon monoxide feed stream, e.g., at least 5% greater than, at least 10% greater than, or at least 25% greater than.

In one embodiment, at least a portion of the carbon monoxide in the purge stream is reacted with at least one of methanol and a methanol derivative in the second reactor under conditions effective to produce additional acetic acid. Preferably, at least a portion of the carbon monoxide in the purge stream and at least a portion of the carbon monoxide in the derivative stream are directed, optionally combined then directed, to a secondary reactor and reacted with at least one of methanol and a methanol derivative, e.g., methyl acetate or dimethyl ether, to produce additional acetic acid. In such embodiments, the amount of total residual carbon monoxide that is converted to additional acetic acid is greater than the amount of total residual carbon monoxide that may be converted in conventional processes that do not convert residual carbon monoxide in both the purge stream and the derivative stream(s), e.g., at least 1% greater, at least 5%, at least 10% greater or at least 25% greater. Accordingly, in some embodiments, less than 10 mol %, e.g., less than 5 mol % or less than 1 mol % of the first and second amounts of residual carbon monoxide, in total, are vented from the process.

In another embodiment, the invention relates to a process for producing acetic acid comprising the step of contacting with at least one of methanol and a methanol derivative a secondary carbon monoxide feed stream, e.g., a secondary low carbon monoxide content feed stream, comprising a low concentration of carbon monoxide (as compared to conventional carbon monoxide feed streams), e.g., from 10 mol % to 95 mol %, from 25 mol % to 75 mol % or from 40 mol % to 60 mol % carbon monoxide. In one embodiment, the secondary carbon monoxide feed stream is the reaction product of a previous carbonylation reaction or a derivative of such a reaction product, which may have been separated, for example, to remove condensable liquids. Preferably, the low carbon monoxide content feed stream comprises from 60 mol % to about 70 mol % carbon monoxide. In terms of partial pressures, the low carbon monoxide content feed streams optionally have a carbon monoxide partial pressure of from 10% to 95% of the total pressure of the derivative stream(s), e.g., from 25% to 75% or from 40% to 60%. In terms of limits, the low carbon monoxide feed stream preferably comprises less than 95 mol % carbon monoxide, e.g., less than 80 mol %, less than 70 mol %, less than 50 mol %, or less than 40 mol %. In other embodiments, the low carbon monoxide feed stream has a carbon monoxide partial pressure less than 95% of the total pressure of the low carbon monoxide feed stream, e.g., less than 80%, less than 70%, less than 50%, or less than 40%. Again, for carbon monoxide to be reacted with methanol to form acetic acid, some amount of carbon monoxide should be present in the carbon monoxide feed stream. For example, the carbon monoxide feed stream may comprise residual carbon monoxide in an amount greater than 0.1 mol %, greater than 0.5 mol % or greater than 1 mol %; or the carbon monoxide feed stream may have a carbon monoxide partial pressure greater than 0.1% of the total pressure of the low carbon monoxide feed stream, e.g., greater than 0.5% or greater than 1%. The carbon monoxide feed stream may further comprise, for example, methanol and/or a methanol derivative, e.g., methyl acetate or dimethyl ether, which is used to produce an acetic acid composition. The inventive process reacts low carbon monoxide feed streams, optionally obtained from vented gases, and thus avoids the waste thereof. Preferably, the contacting step is performed in a fixed bed reactor or a trickle bed reactor and over a catalyst, e.g., a solid phase metal catalyst, which may be fixed in a catalyst bed. The catalyst may be specifically selected for use with the low concentration carbon monoxide feed stream.

In another embodiment, the invention is to a process for producing acetic acid comprising the step of contacting a secondary carbon monoxide feed stream having a carbon monoxide partial pressure of less than 95% of the total pressure the carbon monoxide feed stream, e.g., less than 90%, less than 80%, less than 70%, less than 50%, or less than 40%, with at least one of methanol and a methanol derivative to produce an acetic acid composition. Thus, this embodiment of the invention utilizes a secondary feed stream having a partial pressure of carbon monoxide lower than conventional processes, e.g., at least 5% lower, at least 10% lower, at least 20% lower, or at least 50% lower. In one embodiment, the secondary carbon monoxide feed stream is the reaction product of a previous carbonylation reaction or a derivative of such a reaction product, which may have been separated, for example, to remove condensable liquids. Preferably, the contacting is performed over a solid phase metal catalyst. As noted above, for carbon monoxide to be reacted with methanol to form acetic acid, some amount of carbon monoxide should be present in the carbon monoxide feed stream. Advantageously, this process has the capability to utilize carbon monoxide streams that are less pure than conventional carbon monoxide feed streams.

Also, an additional embodiment relates to a process for producing acetic acid comprising the step of contacting a carbon monoxide feed and at least one of methanol and a methanol derivative under conditions effective to produce a reaction product comprising a crude acetic acid product and a separation vent stream. The separation vent stream, in one embodiment, results from the separation of the crude acetic acid product. The separation vent stream comprises low amounts of carbon monoxide, e.g., less than 60 mol %, e.g., less than 50 mol %, less than 25 mol %; less than 10 mol %; less than 5 mol %; or less than 1 mol %. In terms of ranges, the separation vent stream may comprise from 0.1 mol % to 60 mol % carbon monoxide, e.g., from 1 mol % to 50 mol %, or from 5 mol % to 25 mol %. In another embodiment, the separation vent stream has a carbon monoxide partial pressure less than 60% of the total pressure of the vent stream, e.g., less than 50%, less than 25%, less than 10%, less than 5%, or less than 1%. As such, less carbon monoxide is wasted through venting in the purification train and the overall carbon monoxide conversion may be advantageously improved. In one embodiment, the overall carbon monoxide conversion relates to the conversion of the initial carbon monoxide feed stream in a first reaction and the conversion of residual carbon monoxide in a second reaction. Overall carbon monoxide conversions, are preferably greater than 90%, e.g., greater than 95%, greater than 99%, or greater than 99.5%.

Carbonylation

The features of the present invention may be applied to any suitable methanol carbonylation process. The formation of acetic acid via a carbon monoxide/methanol carbonylation reaction may be carried out by reacting methanol and/or methanol derivatives with carbon monoxide. Exemplary carbonylation systems 100 are shown in FIGS. 1-5. Carbonylation systems 100 comprise carbonylation reaction zone 101, separation zone 102 and a secondary reaction zone 103. Other exemplary carbonylation systems, including reaction zone and separation zones, that may be used with embodiments of the present invention include those described in U.S. Pat. Nos. 7,223,886, 7,005,541, 6,6657,078, 6,339,171, 5,731,252, 5,144,068, 5,026,908, 5,001,259, 4,994,608, and U.S. Pub. Nos. 2008/0287706, 2008/0293966, 2009/0107833, 2009/0270651, the entire contents and disclosures of which are hereby incorporated by reference. Exemplary reaction zone 101 and separation zone 102 are shown in the detailed schematic diagrams discussed below with respect to FIGS. 3-5.

As shown in FIGS. 1-5, methanol feed stream 104 and carbon monoxide feed stream 105 are fed, preferably continuously fed, to reaction zone 101 to produce a crude acetic acid product 106. Crude acetic acid product 106 may be fed to the separation zone 102 which produces a purified acetic acid product 107 and derivative streams 108 and 109, and optional derivative stream 110. Derivative stream 108 may be fed to secondary reaction zone 103. Derivative stream 109, which may comprise recycled compounds, may be fed to reaction zone 101. In optional embodiments, optional derivative stream 110 may also be fed to secondary reaction zone 103. In one embodiment, the derivative stream(s) are streams that are derived from the crude acetic acid product. For example, the derivative stream(s) may be streams that result from the separation of the crude acetic acid product. As another example, the derivative streams may be stream(s) yielded by flasher 131. In one embodiment, the derivative stream(s) do not include conventional off-gas streams. As noted above, conventional off-gas streams are streams of by-product gases that build up in the reactor as the crude acetic acid product is withdrawn, e.g., withdrawn into a flasher. These off-gas streams essentially comprise reaction by-products and carbon monoxide, and do not result from the separation of the crude acetic acid product. Thus, conventional off-gas streams are not considered to be derivative streams.

Because the present invention provides for efficient utilization of residual carbon monoxide, e.g., the residual carbon monoxide in the derivative stream(s), the inventive processes and systems allow larger amounts of off-gas to be withdrawn from the reactor and/or the flasher. These larger amounts of off-gas may beneficially be used to supplement other streams throughout the carbonylation/separation process, e.g., for catalyst stabilization, for recycle streams, or for pump-around streams. In conventional systems, without secondary conversion of residual carbon monoxide in derivative stream(s), larger amounts of off-gas purged would merely result in increased waste of carbon monoxide, which would lower overall carbon monoxide efficiencies. The utilization of the residual carbon monoxide in the derivative stream(s) allows a larger off-gas purge while still maintaining acceptable overall carbon monoxide efficiencies, e.g., without lowering overall carbon monoxide efficiencies.

Figure 2:
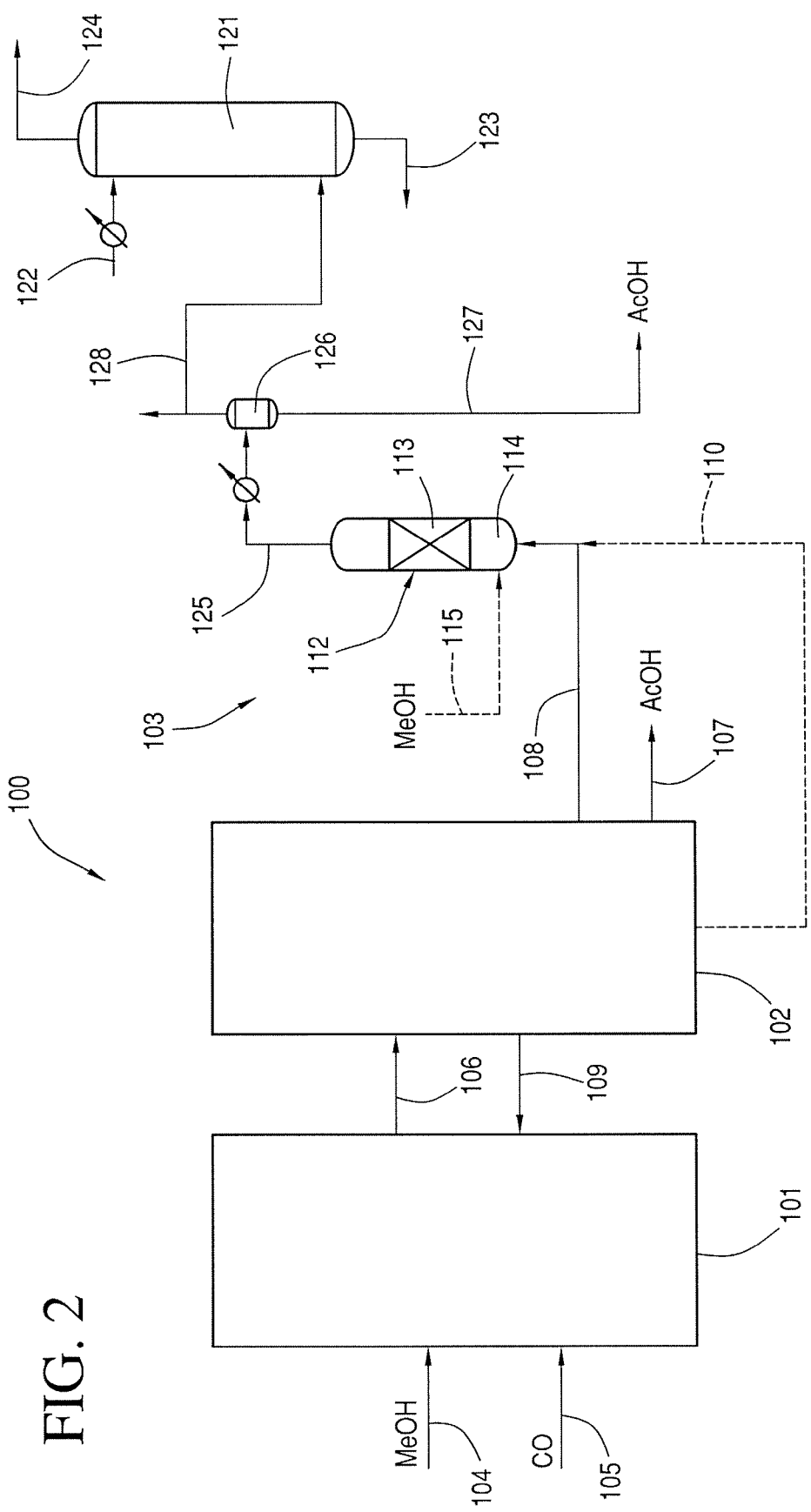
FIG. 2 is a schematic diagram of an exemplary low pressure gas phase carbonylation secondary reactor for processing a purged derivative stream from an acetic acid purification section in accordance with an embodiment of the present invention.

Derivative stream 108 may be in the liquid-phase or vapor-phase and preferably comprises dissolved and/or entrained residual carbon monoxide and optionally methanol and/or its reactive derivatives, preferably methyl acetate. In preferred embodiments, derivative stream 108 is in the vapor-phase. In FIG. 1, derivative stream 108 is fed to secondary reactor 111, which preferably is a high pressure liquid phase carbonylation secondary reactor. In FIG. 2, derivative stream 108 is fed to secondary reactor 112, which preferably is a low pressure gas phase carbonylation secondary reactor.

The process conditions for the supplemental carbonylation reaction in the secondary reactors 111, 112 may vary widely. The reaction may be conducted over a homogeneous or heterogeneous catalyst, e.g. a solid phase metal catalyst. The secondary carbonylation reaction may be a homogeneous reaction or a heterogeneous reaction. In one embodiment, the catalyst may be similar to the catalyst used for the carbonylation reaction in reaction zone 101, discussed further below. In another embodiment, the catalyst may be a liquid phase catalyst. Also, the reaction in the second reactor (and optionally that in the first reactor, as well) may be conducted in a counter-current or co-current manner, with a vapor phase co-current reaction being preferred. Although the catalyst for the reaction in the secondary reactors 111, 112 may be the same as the catalyst in the reaction zone 101, it is preferred that the catalyst in the secondary reactors 111, 112 are different from the catalyst in the reaction zone 101. Preferably, the catalyst in the secondary reactors 111, 112 is tailored to account for a carbon monoxide stream that comprises lower amounts of carbon monoxide. Preferably, the catalyst in the second reactor is a rhodium diiodide dicarbonyl anion that is ionically bound to a suitable resin, e.g., polyvinylpyridine or carbon.

The secondary reactors 111, 112, generally, may be any reactor suitable for carbonylation of methanol with a relatively low carbon monoxide feed stream. In preferred embodiments, the secondary reactors 111, 112 are each independently a trickle bed reactor and/or a fixed bed reactor. Trickle bed reactors and fixed bed reactors preferably comprise a solid phase metal catalyst fixed or packed in a catalyst bed. In one embodiment, each of the secondary reactors 111, 112 may comprise catalyst section 113 and a head space 114.

Derivative stream 108 fed to the secondary reaction zone 103 preferably comprises a relatively lower concentration of carbon monoxide than is fed to the carbonylation reaction zone 101. In one embodiment, the concentration of carbon monoxide in derivative stream 108 may be at least 5% lower than the concentration of the carbon monoxide fed to the reaction zone 101, e.g., at least 10% lower, at least 25% lower, or at least 50% lower. In other embodiments, the carbon monoxide concentration of derivative stream 108 (either in mol % or carbon monoxide partial pressure) may be at least 5% lower than the concentration in a conventional off-gas stream, e.g., at least 10% lower, at least 25% lower, or at least 50% lower. In one embodiment, because of the relatively low amount of carbon monoxide in the feed, the molar ratio of other reactants, e.g., methanol and/or methanol derivatives, to carbon monoxide in the second reactor is greater than 0.02:1, e.g., greater than 0.1:1, greater than 0.25:1 or greater than 0.5:1.

In preferred embodiments, the reactant, e.g., methanol and/or methanol derivatives, reacted in the secondary reactors 111, 112, may be present in derivative stream 108. In one embodiment, derivative stream 108 comprises methanol and/or methanol derivative in an amount ranging from 5 mol % to 90 mol %, e.g., from 25 mol % to 75 mol % or from 40 mol % to 60 mol %. In other embodiments, derivative stream 108 is in the vapor phase and has a methanol and/or methanol derivative partial pressure of from 10% to 90% of the total pressure of derivative stream 108, e.g., from 25% to 75% of from 40% to 60%. In preferred embodiments the methanol and/or methanol derivative reactant in secondary reactors 111, 112 is methyl acetate. In optional embodiments, fresh methanol and/or methanol derivatives may be fed to secondary reactors 111, 112, via line 115. In other optional embodiments, methanol and/or methanol derivatives contained in the optional derivative stream 110 from the separation zone 102 may be fed to secondary reactors 111, 112, as shown in FIGS. 1 and 2, respectively. In other embodiments, derivative stream 108 comprises acetaldehyde. In these embodiments, secondary reactor 111 may react the acetaldehyde in derivative stream 108 to form other materials. For example, the acetaldehyde may be reacted to form ethanol, which may then be converted to propionic acid, which is easily removed from the product stream. By converting the acetaldehyde in derivative stream 108, acetaldehyde is advantageously removed from derivative stream 108. This reaction of acetaldehyde lowers the amount of acetaldehyde in the product stream and lessens the need for subsequent acetaldehyde removal units, e.g., PRS units.

In FIG. 1, secondary reactor 111 preferably is a high pressure liquid phase carbonylation secondary reactor. The supplemental carbonylation reaction in the secondary reactor 111 may be conducted over a liquid-phase homogeneous catalyst or a solid heterogeneous catalyst. In one embodiment, the liquid-phase homogeneous catalyst comprises metal dissolved in a solution, e.g., rhodium and/or iridium dissolved in acetic acid. In one embodiment, the reaction in secondary reactor 111 is carried out at a pressure of from 0.1 MPa to 10 MPa, e.g., from 1 MPa to 5 MPa or from 2 MPa to 3 MPa and a temperature of from 100° C. to 350° C., e.g., 150° C. to 300° C. or 175° C. to 250° C. Secondary reactor 111 is preferably operated at lower pressure than that of the primary reactor. In one embodiment, secondary reactor 111 is operated at a temperature similar to that of the primary reactor. In other embodiment, secondary reactor 11 is operated at a temperature that is higher, e.g., at least 5% higher or at least 10% higher, than the temperature of the primary reactor.

Derivative stream 108 is preferably fed to secondary reactor 111 as a liquid or as a condensed vapor stream, optionally with fresh reactants 115, to produce a secondary crude product stream 116 that comprises acetic acid and overhead stream 117. Overhead stream 117 comprises methyl iodide, residual carbon monoxide, vaporized methanol, vaporized methyl acetate, and other non-condensable gases such as methane. Overhead stream 117 is condensed and fed to a knock-out pot 118 to remove a liquid stream 119 and a vapor stream 120. Liquid stream 119, along with optional derivative stream 110, is sprayed on the catalyst section 114 in secondary reactor 111.

Secondary crude product stream 116 may be processed further and fed to the separation zone 102 or may be combined with the purified acetic acid product 107. In some embodiments, secondary crude product stream 116 may be recovered independently of purified acetic acid product 107. Preferably, the secondary crude product stream 116 is enriched in acetic acid relative to derivative stream 108. In one embodiment, secondary crude product stream 116 comprises from 30 mol % to 95 mol % acetic acid, e.g., from 50 mol % to 75 mol % or from 45 mol % to 70 mol %. In terms of limits, secondary crude product stream 116 comprises at least 25 mol % acetic acid, e.g., at least 50 mol %, at least 40 mol % or at least 60 mol %. In terms of partial pressures, secondary crude product stream 116 (when in the vapor phase) may have an acetic acid partial pressure of from 30% to 95% of the total pressure of secondary crude product stream 116, e.g., from 50% to 75% or from 45% to 70%. In one embodiment, secondary crude product stream 116 may further comprise low amounts of carbon monoxide, e.g., less than 40 mol % carbon monoxide, e.g., less than 25 mol %, less than 10 mol %, less than 5 mol %, or less than 3 mol %. In other embodiments, secondary crude product stream 116 may further comprise methanol and/or methanol derivatives in an amount less than 50 mol %, e.g., less than 40 mol %, less than 25 mol % or less than 15 mol %. In terms of ranges secondary crude product stream 116 may comprise from 10 mol % to 50 mol % methanol and/or methanol derivative, e.g., from 10 mol % to 40 mol %, or from 15 mol % to 30 mol %.

Vapor stream 120 may be purged or flared as shown. In preferred embodiments, vapor stream 120 comprises substantially less carbon monoxide, and more preferably essentially no carbon monoxide, than derivative stream 108. In addition, a portion of vapor stream 120 may be fed to one or more recovery unit 121. As shown in FIG. 1, there is provided one recovery unit 121. A scrubbing solvent 122, preferably chilled to less than 25° C., may be fed to recovery unit 121 to scrub vapor stream 120 of low boiling point components, such as methyl iodide, which are removed via line 123 and are preferably returned to the reaction zone 101. Exemplary scrubbing solvents include methanol, methyl acetate, dimethyl ether, acetic acid and mixtures thereof. The overheads of recovery unit 121 may exited as purge gas 124.

In FIG. 2, secondary reactor 112 preferably is a low pressure gas phase carbonylation secondary reactor. The supplemental carbonylation reaction in the secondary reactor 112 may be reacted with a heterogeneous catalyst. In one embodiment, the reaction in the secondary reactor is carried out at a pressure of from 0.01 MPa to 10 MPa, e.g., 0.05 MPa to 5 MPa or 0.05 MPa to 1 MPa and a temperature of from 150° C. to 350° C., e.g., 150° C. to 300° C. or 175° C. to 250° C. By conducting the reaction in the secondary reactor at lower pressures, the burden on system components, e.g., pumps and compressors, may be reduced. Also, because lower temperature and/or lower pressure operation is less corrosive, vessels need not be made from expensive corrosion-resistant metals and less-expensive metals, e.g., standard stainless steel, may be used.

The derivative stream 108 is preferably fed to secondary reactor 112 as a vapor, optionally with derivative stream 110, to produce a secondary crude product stream 125. In optional embodiment, fresh reactants may be added to head space 114 of the secondary reactor 112. The secondary crude product stream 125 is condensed and fed to knock-out pot 126 to remove a liquid stream 127 comprising acetic acid and a vapor stream 128. Liquid stream 127 may be processed further and fed to the separation zone 102 or may be combined with the purified acetic acid product 107. In some embodiments, secondary crude product stream 125 may be recovered independently of purified acetic acid product 107. Preferably, liquid stream 127 is enriched in acetic acid relative derivative stream 108. In one embodiment liquid stream 127 comprises from 30 mol % to 95 mol % acetic acid, e.g., from 50 mol % to 75 mol % or from 45 mol % to 70 mol %. In terms of limits, stream 127 comprises at least 25 mol % acetic acid, e.g., at least 50 mol %, at least 40 mol % or at least 60 mol %. In one embodiment, stream 127 may further comprise low amounts of carbon monoxide, e.g., less than 40 mol % carbon monoxide, less than 25 mol %, less than 10 mol %, less than 5 mol %, or less than 3 mol %. In other embodiments, stream 127 may further comprise methanol and/or methanol derivatives in an amount less than 50 mol %, e.g., less than 40 mol %, less than 25 mol % or less than 15 mol %. In terms of ranges, stream 127 may comprise from 10 mol % to 50 mol % methanol and/or methanol derivative, e.g., from 10 mol % to 40 mol %, or from 15 mol % to 30 mol %.

In some embodiments, where the secondary reaction is conducted in the vapor phase, the reaction temperature may be maintained at a temperature below the dew point of acetic acid. In such cases, the resultant acetic acid product will contain an amount of rhodium. This amount of rhodium may be greater than the amount of rhodium, if any, in conventional acetic acid products that do not use the inventive processes and/or systems.

Vapor stream 128 in FIG. 2 may be purged or flared as shown. In preferred embodiments, vapor stream 128 comprises substantially less carbon monoxide, and more preferably comprises essentially no carbon monoxide, than derivative stream 108. In addition, a portion of vapor stream 128 may be fed to one or more recovery unit 121, as discussed above with reference to FIG. 1.

Figure 3:
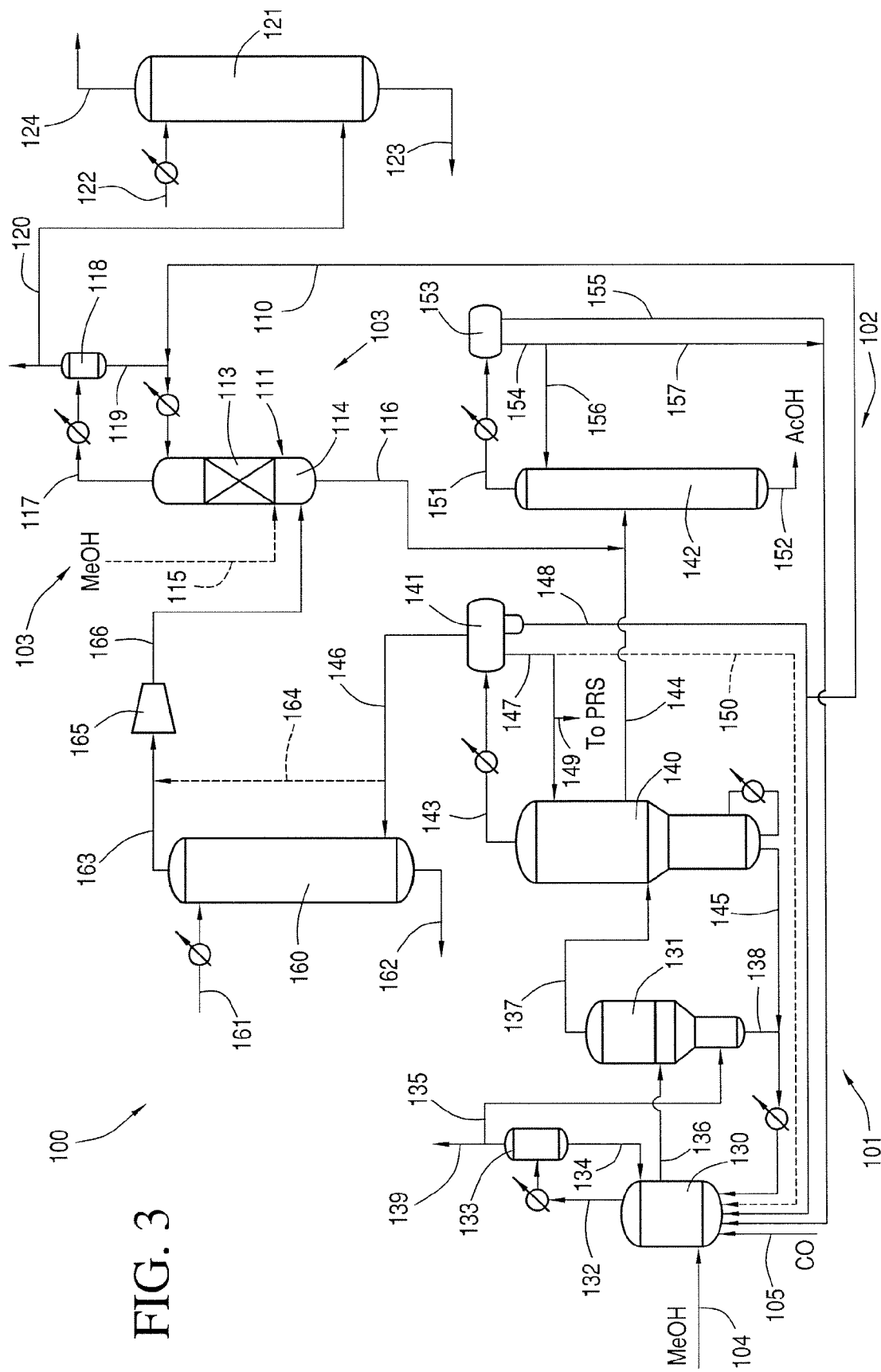
FIG. 3 is a detailed schematic diagram of an exemplary high pressure liquid phase carbonylation secondary reactor for processing a purged derivative stream from an acetic acid purification section in accordance with an embodiment of the present invention.
Figure 4:
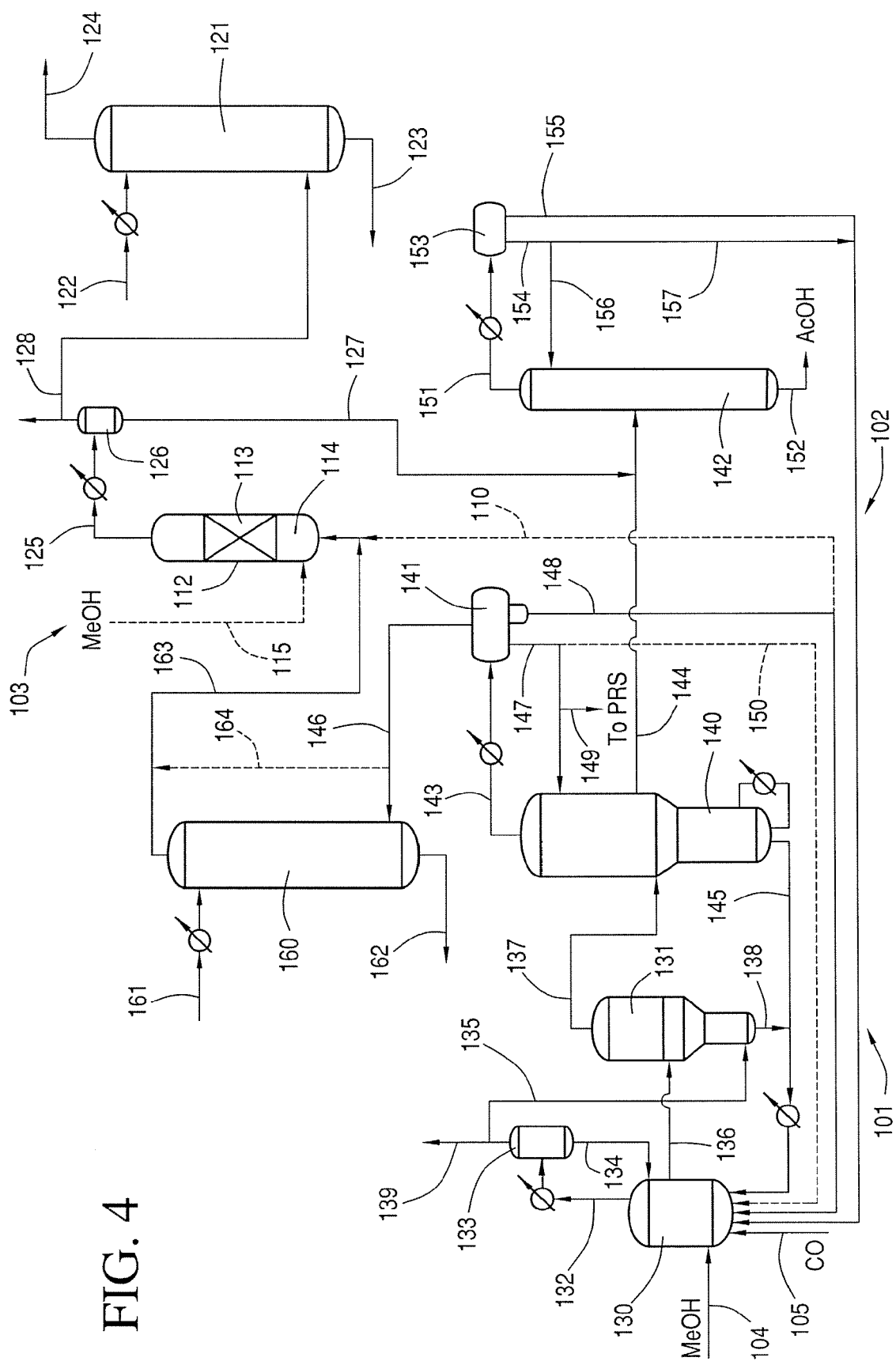
FIG. 4 is a detailed schematic diagram of an exemplary low pressure gas phase carbonylation secondary reaction for processing a purged derivative stream from an acetic acid purification section in accordance with an embodiment of the present invention.
Figure 5:
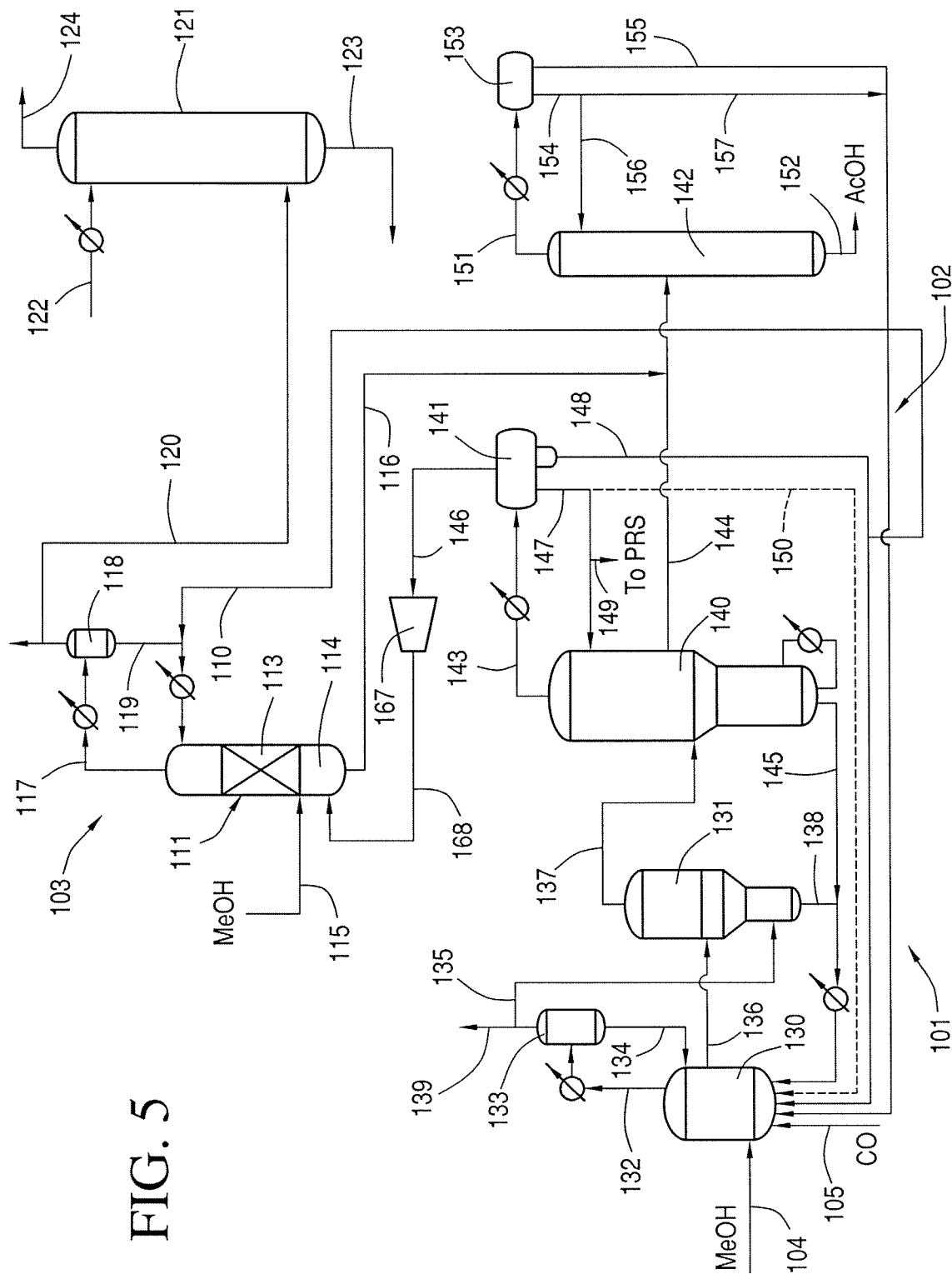
FIG. 5 is a schematic diagram of an exemplary acetic acid reaction process, which includes reaction and separation, in accordance with an embodiment of the present invention.

Returning to the reaction zone, an exemplary reaction zone 101 is shown in FIGS. 3-5. Reaction zone 101 comprises a first reactor 130, flasher 131 and a reactor recovery unit 132. In some embodiments of the present invention, the primary carbonylation reaction is conducted in first reactor 130. Low purity carbon monoxide feed stream 105 has the characteristics discussed above. In one embodiment, the carbonylation is achieved by reacting carbon monoxide with methanol in first reactor 130, e.g., a continuous stirred tank reactor ("CSTR").

When using a CSTR, the catalyst is dissolved in the reaction solvent and liquid methanol and carbon monoxide gas are injected from the bottom as reaction raw materials and made to react with one another. When a CSTR is utilized, the CSTR may be adapted to agitate the reaction solution by an agitation device such as an impeller. Alternatively, a bubble column reactor may be utilized as the first reactor to perform the carbonylation. When a bubble column reactor is utilized, a cylindrical reactor is filled with a reaction solvent and a solid catalyst. Liquid methanol is supplied from the bottom as reaction raw material while carbon monoxide gas is injected upward from the bottom as jet stream. The injected carbon monoxide gas forms bubbles as it rises in the liquid contained in the cylindrical reactor and particles of the catalyst are also driven to move upward in the cylindrical reactor by the gas lift effect and dispersed into the liquid. As one example, the carbon monoxide may be injected into the liquid contained in a cylindrical reactor as jet stream by way of a nozzle arranged at the bottom of the cylindrical reactor for the purpose of mobilizing particles of the solid catalyst in the reactor, as disclosed in Japanese Patent Application Laid-Open No. 6-340242, the disclosure of which is hereby incorporated by reference. In another embodiment, a plurality of primary reactors may be used and the various configurations of primary reactors are considered to be within the scope of the present invention. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference in its entirety.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, ($1^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

An alkyl halide co-catalyst/promoter is generally used in combination with the Group VIII metal catalyst component. Methyl iodide is preferred as the alkyl halide promoter. Preferably, the concentration of alkyl halide in the liquid reaction composition is in the range of 1 to 50% by weight, preferably 15 to 25% by weight.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the first reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa Acetic acid is typically manufactured in a liquid phase reaction at a temperature of from about 150-200° C. and a total pressure from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Methanol feed stream 104 preferably comprises methanol and/or reactive derivatives thereof. Suitable reactive derivatives of methanol include methyl acetate, dimethyl ether, and methyl formate. In one embodiment, a mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

Carbon monoxide feed stream 105 is a lower purity carbon monoxide feed stream as described above. Hydrogen may be generated in the carbon monoxide feed stream by the water gas shift reaction. Preferably, the partial pressure of hydrogen is maintained at a low level, for example, less than 0.1 MPa or less than 0.05 MPa, as its presence may result in the formation of various hydrogenation products. In one embodiment, the partial pressure of carbon monoxide in the reaction is in the range of from 0.1 MPa to 7 MPa, e.g., from 0.1 MPa to 3.5 MPa, or from 0.1 MPa to 1.5 MPa.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. %.

In accordance with a preferred carbonylation process according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through an acetic acid solvent reaction medium containing the catalyst e.g., rhodium or iridium, methyl iodide promoter, methyl acetate, and/or additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

First reactor 130 is preferably either a stirred vessel, e.g., CSTR, or bubble-column type vessel, with or without an agitator, within which the reaction medium is maintained, preferably automatically, at a predetermined level. This predetermined level may remain substantially constant during normal operation. Into first reactor 130, methanol, carbon monoxide, and sufficient water may be continuously introduced as needed to maintain at least a finite concentration of water in the reaction medium.

In one embodiment, carbon monoxide, e.g., in the gaseous state, is continuously introduced into first reactor 130, desirably below the agitator, which is used to stir the contents. The temperature of first reactor 130 may be controlled, as indicated above. Carbon monoxide feed 105 is introduced at a rate sufficient to maintain the desired total reactor pressure.

The gaseous feed is preferably thoroughly dispersed through the reaction medium by the stirring means. A carbon monoxide purge stream, e.g., an off-gas, 132 is purged from first reactor 130. Purge stream 132 prevents buildup of impurities remaining from the carbon monoxide feed, e.g., inerts, and gaseous by-products, e.g., methane, carbon dioxide, and hydrogen, and also maintains a set carbon monoxide partial pressure at a given total reactor pressure. Purge stream 132 is not a derivative stream, as discussed above. Purge stream 132, advantageously, is larger than conventional purge streams, e.g., off-gas streams. In one embodiment, purge stream 132 comprises a higher volume percentage of carbon monoxide, as compared to conventional purge streams, although, in other embodiments, the volume percentage of carbon monoxide in purge stream 132 is similar to those of conventional purge streams. As a result of the larger purge streams, the inventive processes are able to provide larger amounts of carbon monoxide for use throughout the carbonylation process, e.g., for catalyst stabilization. These larger amounts of carbon monoxide are achieved without feeding additional carbon monoxide to the system and while still achieving overall carbon monoxide efficiencies equal to or greater than those of conventional carbonylation systems.

As shown in FIGS. 3-5, reactor recovery unit 133 may be utilized to separate impurities from the purge stream in line 132 to form an impurity stream (not shown) and a purified off-gas (not shown). In one embodiment, reactor recovery unit removes low boiling point components from purge stream 132. Of course, other separation methods may be employed to separate and/or purify purge stream 132. Purge stream(s) 132 from first reactor 130 may be combined or scrubbed separately and are typically scrubbed with either acetic acid, methanol, or mixtures of acetic acid and methanol to prevent loss of low boiling components such as methyl iodide from the process. If methanol is used as the purge scrub liquid solvent, the enriched methanol (containing methyl iodide) from reactor recovery unit 133 is typically returned to the process, e.g., via line 134, although it can also be returned into any of the streams that recycle back to the reactor such as the flasher residue or light ends or dehydration column overhead streams. If acetic acid is used as the purge scrub liquid solvent, the enriched acetic acid (containing methyl iodide) from the scrubber is typically stripped of absorbed light ends and the resulting lean acetic acid is recycled back to the scrubber (not shown). The light end components stripped from the enriched acetic acid scrubbing solvent may be returned to the main process directly, e.g., via line 134, or indirectly in several different locations including the first reactor 130, flasher 131, e.g., via line 135, or a suitable area in the separation zone 102. In one embodiment, the stream exiting the top of reactor recovery unit 133 is exited via line 139 to further processing, which may entail, for example, further separation or scrubbing. Preferably, the contents of line 136, which may contain, inter alia, (residual) carbon monoxide and methanol, may be further reacted, preferably in secondary reaction zone 103, to produce additional acetic acid. Optionally, the gaseous purge streams may be vented through the flasher base liquid or lower part of the light ends column to enhance rhodium stability and/or they may be combined with other gaseous process vents (such as the purification column overhead receiver vents) prior to scrubbing.

Purge stream 132 comprises an amount of residual carbon monoxide, e.g., a first amount of residual carbon monoxide. In one embodiment, at least a portion, e.g., an aliquot portion, of purge stream 132 is directed to a reactor, e.g., primary reactor 130, where the residual carbon monoxide may be converted into acetic acid. In other embodiments, purge stream 132 is directed to secondary reactor 113 where the residual carbon monoxide may be converted into acetic acid. In other embodiments, purge stream 132 is directed to a reactor other than primary reactor 130 or secondary reactor 113. In another embodiment, purge stream 132 may be combined with one or more derivative streams that comprise residual carbon monoxide and then directed to primary reactor 130, secondary reactor 113 and/or another reactor. In another embodiment, at least a portion, e.g., an aliquot portion, of purge stream 132 may be directed to separation zone 102, e.g., one or more of the components of separation zone 102, which is configured downstream of first reactor 130. In these cases, as one example, the carbon monoxide in purge stream 132 may be used to stabilize catalyst that may be present in the process streams of separation zone 102. For example, at least a portion of purge stream 132 may be directed to light ends column 140. In another embodiment, at least a portion of purge stream 132 may be directed to flasher 131. In these cases, the at least a portion of purge stream 132 may comprise at least 20 mol % carbon monoxide, e.g., at least 40 mol % or at least 60 mol % In one embodiment, the purge stream 132 is separated into two or more carbon monoxide-containing off-gas streams, each of which may be directed to separation zone 102 and/or to the reactor and/or to flasher 131. In one embodiment, all of purge stream 132 is directed to flasher 131. In one embodiment, all of purge stream 132 is directed to separation zone 102, e.g., one or more of the components of separation zone 102. In one embodiment, a portion of purge stream 132 may be directed to flasher 131 and another portion of purge stream 132 may be directed to secondary reactor 113 and/or another reactor.

The crude acetic acid product comprises an amount of unreacted carbon monoxide, e.g., a second amount of residual carbon monoxide. As noted above, in some embodiments, the acetic acid in the crude acetic acid product is separated into purified acetic acid and at least one, e.g., at least two or at least three, derivative streams. In preferred embodiments, at least one, e.g., at least two or at least three, of these derivative streams comprises residual carbon monoxide. The derivative stream comprising residual carbon monoxide may be beneficially further reacted to form additional acetic acid.

The crude acetic acid product is drawn off from the first reactor 130 at a rate sufficient to maintain a constant level therein and is provided to flasher 131 via stream 136. In flasher 131, the crude product is separated in a flash separation step to obtain a volatile ("vapor") overhead stream 137 comprising acetic acid and a less volatile stream 138 comprising a catalyst-containing solution. The catalyst-containing solution comprises acetic acid containing the rhodium and the iodide salt along with lesser quantities of methyl acetate, methyl iodide, and water. The less volatile stream 138 preferably is recycled to reactor 130. Vapor overhead stream 137 also comprises methyl iodide, methyl acetate, water, PRCs. Dissolved and/or entrained gases exit first reactor 130 and enter flasher 131 comprise a portion of the carbon monoxide and may also contain gaseous by-products such as methane, hydrogen, and carbon dioxide. The dissolved gases exit the flasher 131 as part of overhead stream 137. In some embodiments, the low-boiling overhead vapor stream 137 may be fed to the secondary reaction zone 103, e.g., to the secondary reactor.

Overhead stream 137 from flasher 131 is directed to separation zone 102. Separation zone 102 comprises light ends column 140, decanter 141, and drying column 142. Additionally, separation zone 102 may also comprise one or more columns for removing permanganate reducing compounds ("PRCs"), guard beds, heavy ends columns, extractors, etc.

In light ends column 140, stream 137 yields a low-boiling overhead vapor stream 143, a purified acetic acid product that preferably is removed via a side stream 144, and a high boiling residue stream 145. Acetic acid removed via side stream 144 preferably is subjected to further purification, such as in drying column 142 for selective separation of acetic acid from water and/or an optional heavy ends column (not shown), as described in U.S. Pat. No. 6,627,770, the entirety of which is hereby incorporated by reference. Preferably, side stream 144 and residue stream 145 comprise substantially no carbon monoxide or no detectable amounts of carbon monoxide.

The low-boiling overhead vapor in line 143 may comprise dissolved and/or entrained carbon monoxide; methyl iodide; methyl acetate; hydrogen; water; PRCs; acetic acid; inerts such as nitrogen, argon, and helium; and other dissolved gases. In terms of upper limits, the low-boiling overhead vapor in line 143 may comprise less than 75 mol % carbon monoxide, e.g., less than 60 mol %; less than 50 mol %, or less than 40 mol %; and/or may have a carbon monoxide partial pressure less than 75% of the total pressure of the low-boiling overhead vapor, e.g., less than 60%, less than 50%, or less than 40%. Preferably, the amount of dissolved and/or entrained carbon monoxide in line 143 preferably is less than the amount of carbon monoxide in feed stream 105, e.g., at least 5% less, at least 10% less, at least 25% less, or at least 50% less. In terms of ranges, the amount of carbon monoxide in line 143 may range from 10 mol % to 75 mol %, e.g., from 25 mol % to 60 mol %, or from 40 mol % to 50 mol %; or the carbon monoxide partial pressure may range from 10% to 75% of the total pressure of low-boiling overhead vapor, e.g., from 25% to 60% of from 40% to 50%. Preferably, the low-boiling overhead vapor in line 143 comprises at least 0.1 mol % carbon monoxide, e.g., at least 0.5 mol %, or at least 1; and/or has a carbon monoxide partial pressure of at least 0.1% of the total pressure of the low-boiling overhead vapor, e.g., at least 0.5% or at least 1%. Also, the low-boiling overhead vapor in stream 143 may comprise at least 0.1 mol % methyl iodide, e.g., at least 1 mol %, or at least 5 mol %. In terms of ranges, stream 143 may comprise from 0.1 mol % to 30 mol % methyl iodide, e.g., from 1 mol % to 25 mol %, or from 5 mol % to 20 mol %. In some embodiments, the derivative stream of the crude acetic acid product in line 143 may be fed to the secondary reaction zone 103.

U.S. Pat. Nos. 6,143,930 and 6,339,171 discloses that there is generally a higher concentration of PRCs, and in particular acetaldehyde, in the low-boiling overhead vapor stream 143 exiting the light ends column 140 than in the high-boiling residue stream 145. In some embodiment, low-boiling overhead vapor stream 140, containing PRCs, optionally may be subjected to additional processing in a PRC removal system ("PRS") (not shown) to reduce and/or remove the amount of PRCs present (or a portion thereof). PRCs are formed during the carbonylation of methanol in the presence of a Group VIII metal carbonylation catalyst. PRCs, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

As shown, low-boiling overhead vapor stream 143, is preferably condensed and directed to an overhead phase separation unit, as shown by overhead receiver decanter 141. Conditions are desirably maintained in the process such that low-boiling overhead vapor stream 143, once in decanter 141, will separate into a light phase and a heavy phase. Generally, low-boiling overhead vapor stream 143 is cooled to a temperature sufficient to condense and separate the condensable methyl iodide, methyl acetate, acetaldehyde and other carbonyl components, and water into two phases. A gaseous portion of stream 143 may include carbon monoxide, and other noncondensable gases such as methyl iodide, carbon dioxide, hydrogen, and the like and is vented from the decanter 141 via line 146. Line 146 preferably has a partial pressure of carbon monoxide of less than 95% of the total pressure of line 146, e.g., less than 80%; less than 75%; less than 60%; less than 50%; or less than 40%. As used herein, all partial pressures are based upon the total pressure of all non-condensable components in the specified stream or vessel. Additionally or alternatively, line 146 may comprise less than 95 mol % carbon monoxide, e.g., less than 80 mol %; less than 75 mol %; less than 60 mol %; less than 50 mol %; or less than 40 mol %. Line 146 preferably has a carbon monoxide partial pressure and/or a weight percentage that is lower than carbon monoxide feed stream 105, which feeds first reactor 130, e.g., 5% lower; 10% lower; 25% lower or 50% lower. In terms of ranges, the amount of carbon monoxide in line 146 optionally ranges from 10 mol % to 95 mol %, e.g., from 25 mol % to 75 mol %, or from 40 mol % to 60 mol %. Optionally, line 146 has a carbon monoxide partial pressure of from 10% to 95% of the total pressure of line 146, e.g., from 25% to 75% or from 40% to 60%. Line 146 preferably has a mole percentage of methyl acetate that optionally ranges from 10 mol % to 60 mol %, e.g., from 15 mol % to 50 mol %, or from 25 mol % to 45 mol %; and/or a methyl acetate partial pressure of from 10% to 60% of the total pressure of line 146, e.g., from 15% to 50% or from 25% to 45%. This derivative stream in line 146 comprising carbon monoxide may be directed to a secondary reaction zone 103, for reaction with methanol to form additional acetic acid, as discussed above in FIGS. 1 and 2.

The condensed light phase 147 in decanter 141 preferably comprises water, acetic acid, and PRCs, as well as quantities of methyl iodide and methyl acetate. The condensed heavy phase 148 in decanter 141 will generally comprise methyl iodide, methyl acetate, and PRCs. The condensed heavy liquid phase 148 in the decanter 141 can be conveniently recirculated, either directly or indirectly, to the reactor 130. For example, a portion of this condensed heavy liquid phase 148 can be recirculated to the reactor, with a slip stream (not shown), generally a small amount, e.g., from 5 to 40 mol. %, or from 5 to 20 mol. %, of the heavy liquid phase being directed to a PRS. This slip stream of the heavy liquid phase 148 may be treated individually or may be combined with the condensed light liquid phase 147 for further distillation and extraction of carbonyl impurities in accordance with one embodiment of the present invention.

As shown in FIGS. 3-5, the light phase exits decanter 141 via stream 147. A first portion, e.g., aliquot portion, of light phase stream 147 may be recycled to the top of the light ends column 140 as a reflux stream. A second portion, e.g., aliquot portion, of light phase stream 147 may be directed to the optional PRS (not shown), e.g., as shown by stream 149. A third portion, e.g., aliquot portion, of the light phase stream 147 optionally may be recycled to reactor 130, e.g., as shown by optional recycle stream 150, when additional water is desired or needed in reactor 130. In preferred aspects the water level in the reactor is maintained at a desired level without recycling stream 150 to reactor 130 since recycling stream 150 to the reactor 130 undesirably will result in the recycle of acetic acid and unnecessarily increasing the load on reactor 130.

Light ends column 140 also preferably forms a residuum or bottoms stream 145, which comprises primarily acetic acid and water. Since light ends bottoms stream 145 typically will comprise some residual catalyst, it may be beneficial to recycle all or a portion of the light ends bottoms stream 145 to reactor 130, as shown by optional line 150. Preferably, the light ends bottoms stream 145 may be combined with catalyst phase 138 from flasher 131 and returned together to reactor 130.

As indicated above, in addition to the overhead phase, the light ends column 140 also forms an acetic acid side stream 144, which preferably comprises primarily acetic acid and water. Optionally, a portion of side stream 144 may be recirculated to the light ends column, preferably to a point below where side stream 144 was removed from light ends column, as described in US Pub. No. 2008/0287706, the entirety of which is hereby incorporated by reference.

Since side stream 144 contains water in addition to acetic acid, side stream 144 from the light ends column 140 preferably is directed to a drying column 142, in which the acetic acid and water are separated from one another. As shown, drying column 142, separates acetic acid side stream 144 into an overhead stream 151 comprised primarily of water and a bottoms stream 152 comprised primarily of purified, dried acetic acid. Overhead stream 151 preferably is cooled and condensed in a phase separation unit, e.g., decanter 153, to form a light phase 154 and a heavy phase 155. As shown, a portion of the light phase 154 is refluxed, as shown by stream 156 and the remainder of the light phase is returned to the reactor 130, as shown by stream 157. The heavy phase, which typically is an emulsion comprising water and methyl iodide, preferably is returned in its entirety to the reactor 130, as shown by stream 155, optionally after being combined with stream 157, although a portion may also be further processed (not shown).

The drying column bottoms stream 152 preferably comprises or consists essentially of acetic acid. In preferred embodiments, the drying column bottoms stream comprises acetic acid in an amount greater than 90 mol %, e.g., greater than 95 mol % or greater than 98 mol %. Optionally, the drying column bottoms stream 152 may be further processed, in a heavy ends column (not shown) or iodide guard bed (not shown), prior to being stored or transported for commercial use. Of course, the separation systems of FIGS. 3-5, are merely examples of separation schemes that may be utilized in the present invention. Other combinations of separation units may just as easily be utilized. Preferable separation systems are those wherein at least a portion of residual carbon monoxide is separated and/or recovered from the crude acetic acid product.

Returning to vent gas stream 146 from the overhead decanter 141 of the light ends column 140. In a preferred embodiment, vent gas stream 146, which comprises an amount of residual carbon monoxide, may be directed to secondary reaction zone 103. In FIGS. 3 and 4, the vent gas stream 146 is initially processed in a recovery unit 160 to remove any low boiling point compounds, such as methyl iodide.

A scrubbing solvent 161, preferably chilled to less than 25° C., may be fed to recovery unit 160 to scrub vapor stream 146 of low boiling point components, such as methyl iodide, which are removed via line 162 and are preferably returned to the reaction zone 101. Scrubbing solvents include methanol, methyl acetate, dimethyl ether, acetic acid and mixtures thereof. The overheads of recovery unit 160 may exited as purge gas 163. In one optional embodiment, a portion of the vent gas stream 146 may by-pass the recovery unit 160 in line 164 and be combined with the overhead vapor 163.

Scrubbed gas 163 exiting the top of recovery unit 160 comprises carbon monoxide, methyl acetate, and optionally methyl iodide. In preferred embodiments, scrubbed gas 163 passes through compressor 165 to form high pressure derivative stream 166. In preferred embodiments, the total pressure of the vapor in high pressure derivative stream 166 is from 0.1 MPa to 10 MPa, e.g., 0.5 MPa to 5 MPa or 0.5 MPa to 2 MPa. In one embodiment, the scrubbed gas comprises substantially no methyl iodide, which has been removed by recovery unit 160. High pressure derivative stream 166 is fed to the secondary reaction zone 103 in FIG. 3. The secondary reaction zone 103 comprises the secondary reactor 111 as described above in FIG. 1. Secondary crude product stream 116 is returned to separation zone 102 and co-fed with the side stream 144 to drying column 142. Derivative stream 110 from the heavy phase stream 148 may be also fed to the secondary reactor 111 with the liquid stream 119.

In FIG. 4, vent gas stream 146 from the overhead decanter 141 passes through the recovery unit 160 to generate scrubbed gas 163. In one embodiment, scrubbed gas 163 does not pass through a compressor and remains at a relatively lower pressure than high pressure derivative stream 166 in FIG. 3. Scrubbed gas 163 is fed to secondary reaction zone 103. The secondary reaction zone 103 of FIG. 4 comprises the secondary reactor 112 as described above in FIG. 2. Optionally, along with the scrubbed gas 163, fresh reactants in line 115 and derivative stream 110, may also be fed to secondary reactor 112. Secondary reactor 112 generates a secondary crude product stream 125 that is condensed and fed to a knock-out pot 126 to remove a liquid stream 127 comprising acetic acid. Liquid stream 127 is returned to separation zone 102 and co-fed with the side stream 144 to drying column 142.

In FIG. 5, vent gas stream 146 is fed to secondary reaction zone 103. In one embodiment, vent gas stream 146 from the overhead decanter 141 may pass through a compressor 167 to form high pressure derivative stream 168 that is fed directly to a secondary reactor 111 as taught in FIG. 5. In preferred embodiments, the total pressure of the vapor in high pressure derivative stream 168 is from 0.1 MPa to 10 MPa, e.g., 0.5 MPa to 5 MPa or 0.5 MPa to 2 MPa. High pressure derivative stream 168 may comprise a higher amount of methyl iodide relative to the high pressure derivative stream 166 taught in FIG. 3. In alternative embodiments, the vent gas stream 146 may be fed as the derivative stream to a secondary reactor, without being compressed or processed in a recovery unit.

As discussed above, the present invention utilizes the carbon monoxide derivative stream(s) to yield additional acetic acid which improves overall process efficiency. FIGS. 1-5 show various derivative streams that may be utilized in the secondary reaction of the present invention. Of course, other derivative streams that contain carbon monoxide may also be utilized in accordance with the present invention.

In one embodiment, the derivative stream may be derived from an acetic acid production process as described in CN 101439256A, which is incorporated herein by reference. In one embodiment, the process may involve 1) carbonylation of methanol in a carbonylation reactor to form acetic acid and 2) hydrogenating the acetic acid in a hydrogenation reactor with hydrogen derived, at least in part, from a tail gas stream formed either in the carbonylation process or in the hydrogenation process. Carbon monoxide may also be recovered from the tail gas. In one instance, the tail gas comprising carbon monoxide and hydrogen may be derived from the crude acetic acid stream and/or the crude ethanol stream. This tail gas may be employed in accordance with the present invention to make additional acetic acid. Of course, other carbon monoxide-containing derivative streams in the system may also be employed.

In another embodiment, the derivative stream may be derived from an acetic acid process as described in CN1537840, which is incorporated herein by reference. This process may utilize a reaction zone and a separation zone. In some embodiment, the separation zone comprises inter alia a column for separating water, methyl iodide, and acetic acid; a phase separator; and a rectifying column. Any suitable carbon monoxide-containing streams, e.g., vent streams, from these processes may be employed in accordance with the present invention to make additional acetic acid.

In another embodiment, the derivative stream may be derived from an acetic acid process as described in U.S. Pat. No. 5,334,755, which is incorporated herein by reference. This process may utilize a reaction zone and a separation zone. In some embodiment, the separation zone comprises inter alia a heat exchanger, a distillation column, and/or a gas-liquid separator. Any suitable carbon monoxide-containing streams, e.g., vent streams, from these processes may be employed in accordance with the present invention to make additional acetic acid.

In one embodiment, the derivative stream may be derived from an acetic acid production process as described in U.S. Pat. No. 6,140,535, which is incorporated by reference herein. This acetic acid production process reacts carbon monoxide with methanol and/or a methanol derivative in a liquid reaction composition comprising (i) an iridium carbonylation catalyst, (ii) a methyl iodide co-catalyst, (iii) a metal promoter selected from the group consisting of ruthenium, osmium, rhenium, cadmium, mercury, zinc, gallium, indium and tungsten; (iv) a finite amount of water at a concentration of less than about 8% by weight; (v) methyl acetate; (vi) acetic acid; and (vii) propionic acid by-product and its precursors. The process further comprises the step of withdrawing liquid reaction composition from the carbonylation reactor and introducing at least part of the withdrawn liquid reaction composition, with or without the addition of heat, to a flash zone to form a vapor fraction comprising water, acetic acid product, propionic acid by-product, methyl acetate, methyl iodide and propionic acid precursors, and a liquid fraction comprising involatile iridium catalyst, involatile optional promoter or promoters, acetic acid and water. The vapour outlet from the flash zone is connected to a first distillation zone provided with an overhead condenser and a decanter. In use, the vapours from the distillation zone are condensed into the decanter and form two phases, a methyl iodide-rich phase and an aqueous phase. The heavy methyl iodide rich phase is recycled to the carbonylation reactor and the lighter aqueous phase is divided; part being used as reflux to the distillation zone and part being recycled to the carbonylation reactor. In this system, any of the process stream(s) that may contain residual carbon monoxide, e.g., a vapor stream that may be withdrawn from the decanter, may be utilized in the secondary reaction zone of the present invention.

In one embodiment, the derivative stream may be derived from an acetic acid production process as described in U.S. Pat. No. 5,391,821, which is incorporated herein by reference. This process may utilize a reaction zone and a separation zone. In some embodiment, the separation zone comprises inter alia a column for separating water, methyl iodide, and acetic acid; a phase separator; and a rectifying column. Any suitable carbon monoxide-containing streams, e.g., vent streams, from these processes may be employed in accordance with the present invention to make additional acetic acid.

In one embodiment, the derivative stream may be derived from an acetic acid production process as described in U.S. Pat. No. 7,678,940, which is incorporated herein by reference. This process produces a carboxylic acid and may utilize a reaction zone and a separation zone. In some embodiment, the separation zone comprises inter alia a catalyst-separating column and a first distillation column. An alcohol or an ester corresponding to the carboxylic acid, e.g., acetic acid, may be fed to the first distillation column. The separation zone may further comprise a second distillation column, a condenser, and/or a phase separator. Any suitable carbon monoxide-containing streams, e.g., vent streams, from these processes may be employed in accordance with the present invention to make additional acetic acid.

In one embodiment, the derivative stream may be derived from an acetic acid production process as described in Jones, J. H. (2002), "*The Cativa™ Process for the Manufacture of Acetic Acid,*" Platinum Metals Review, 44 (3): 94-105 discussed above. Any suitable carbon monoxide-containing streams, e.g., vent streams, from these processes may be employed in accordance with the present invention to make additional acetic acid.

In other embodiments, the derivative stream may be derived from an acetic acid production processes as described in Noriyuki Yoneda and Yasuo Hosono (2004); "*Acetic Acid Process Catalyzed by Ionically Immobilized Rhodium Complex to Solid Resin Support;*" Journal of Chemical Engineering of Japan, Vol. 37, No. 4, the disclosure of which is hereby incorporated by reference. These acetic acid production processes employ an ionically immobilized homogeneous rhodium catalyst in a methanol carbonylation process, e.g., the Monsanto process.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, comprising the steps of:
   (a) reacting a carbon monoxide feed comprising:
      (i) less than 99.5 mol % carbon monoxide; and
      (ii) at least one of methanol and a methanol derivative in a first reactor under conditions effective to produce a crude acetic acid product;
   (b) purging from the first reactor a carbon monoxide purge stream comprising a first amount of residual carbon monoxide and one or more impurities, the first amount being greater than 20 mol %;
   (c) separating the crude acetic acid product into at least one derivative stream, at least one of the at least one derivative stream comprising a second amount of residual carbon monoxide; and
   (d) reacting at least a portion of the second amount of residual carbon monoxide and at least one of methanol and a methanol derivative in a second reactor under conditions effective to produce additional acetic acid.

2. The process of claim 1, wherein the overall carbon monoxide conversion is greater than 95%, based on the total amount of carbon monoxide in the carbon monoxide feed.

3. The process of claim 1, wherein at least a portion of the carbon monoxide in the purge stream is reacted with at least one of methanol and a methanol derivative in the second reactor under conditions effective to produce additional acetic acid.

4. The process of claim 1, further comprising the step of: directing at least a portion of the purge stream to a purification zone configured downstream of the first reactor, wherein the at least a portion of the purge stream comprises at least 20 mol % carbon monoxide.

5. The process of claim 1, further comprising the step of: directing at least a portion of the purge stream to a flasher, wherein the at least a portion of the purge stream comprises at least 20 mol % carbon monoxide.

6. The process of claim 1, further comprising the step of: directing at least a portion of the purge stream to a light ends column, wherein the at least a portion of the purge stream comprises at least 20 mol % carbon monoxide.

7. The process of claim 1, wherein the at least one derivative stream comprising residual carbon monoxide, comprises: from 10 mol % to 95 mol % carbon monoxide; and from 5 mol % to 90 mol % at least one of methanol and a methanol derivative.

8. The process of claim 1, wherein the purging maintains the carbon monoxide partial pressure in the reactor at a predetermined level ranging from 0.13 MPa to 1.1 MPa.

9. The process of claim 1, wherein the purge stream comprises:
   carbon monoxide in an amount ranging from 20 mol % to 95 mol %;
   nitrogen in an amount ranging from 0.5 mol % to 20 mol %;
   methane in an amount ranging from 0.5 mol % to 20 mol %;
   carbon dioxide in an amount ranging from 0.5 mol % to 30 mol %; and
   hydrogen in an amount ranging from 0.5 mol % to 50 mol %.

10. The process of claim 1, wherein the reaction temperature in the second reactor ranges from 100° C. to 350° C.

11. The process of claim 1, wherein the reaction pressure in the second reactor ranges from 0.01 MPa to 10 MPa.

12. The process of claim 1, wherein the second reactor comprises a solid metal catalyst comprising at least one metal selected from the group consisting of rhodium, iridium, ruthenium, nickel, and cobalt.

13. The process of claim 1, wherein the at least one of methanol and a methanol derivative employed in the second reactor is methyl acetate.

14. A process for producing acetic acid, comprising
   (a) reacting a carbon monoxide feed comprising
      (i) less than 99.5 mol % carbon monoxide and
      (ii) at least one of methanol and a methanol derivative in a first reactor under conditions effective to produce a crude acetic acid product;
   (b) separating the crude acetic acid product into at least one derivative stream, at least one of the at least one derivative stream comprising residual carbon monoxide; and
   (c) reacting at least a portion of the residual carbon monoxide and at least one of methanol and a methanol derivative in a second reactor under conditions effective to produce additional acetic acid.

15. The process of claim 14, wherein the overall carbon monoxide conversion is at least 90%.

16. The process of claim 14, wherein the carbon monoxide feed comprises less than 95 mol % carbon monoxide.

17. The process of claim 14, wherein the carbon monoxide feed comprises from 10 mol % to 99.5 mol % carbon monoxide.

18. The process of claim 14, wherein the carbon monoxide feed comprises less than 60 mol % carbon monoxide.

19. The process of claim 14, wherein the carbon monoxide feed comprises from 60 mol % to 70 mol % carbon monoxide.

20. A process for producing acetic acid, comprising
   (a) reacting a carbon monoxide feed comprising:
      (i) less than 99.5 wt % carbon monoxide and
      (ii) at least one of methanol and a methanol derivative in a first reactor under conditions effective to produce a crude acetic acid product;
   (b) withdrawing from the first reactor a purge stream comprising impurities and a first amount of residual carbon monoxide;
   (c) separating the crude acetic acid product into at least one derivative stream, at least one of the at least one derivative stream comprising as second amount of residual carbon monoxide; and
   (d) reacting the first and second amounts of residual carbon monoxide and at least one of methanol and a methanol derivative in a second reactor under conditions effective to produce additional acetic acid.

21. The process of claim 20, wherein the purge stream is combined with the at least one derivative stream to form a combined stream and the combined stream is directed to the second reactor.

22. The process of claim 20, wherein less than 10 mol % of the first and second amounts of residual carbon monoxide, in total, are vented from the process.

* * * * *